(12) United States Patent
Lutnick et al.

(10) Patent No.: US 8,255,168 B2
(45) Date of Patent: Aug. 28, 2012

(54) PRODUCTS AND PROCESSES FOR ANALYZING OCTANE CONTENT

(75) Inventors: Howard W. Lutnick, New York, NY (US); Antonio Papageorgiou, New York, NY (US)

(73) Assignee: CFPH, LLC, New York, NY (US)

( * ) Notice: Subject to any disclaimer, the term of this patent is extended or adjusted under 35 U.S.C. 154(b) by 0 days.

(21) Appl. No.: 13/042,977

(22) Filed: Mar. 8, 2011

(65) Prior Publication Data

US 2011/0161256 A1 Jun. 30, 2011

Related U.S. Application Data

(63) Continuation of application No. 11/856,900, filed on Sep. 18, 2007, now Pat. No. 7,925,449.

(60) Provisional application No. 60/845,343, filed on Sep. 18, 2006.

(51) Int. Cl.
*G01N 30/16* (2006.01)
*G01N 30/38* (2006.01)
*G06F 3/01* (2006.01)

(52) U.S. Cl. ............... 702/23; 702/24; 702/31; 702/182

(58) Field of Classification Search .............. 702/22, 702/23, 30, 85, 90, 127, 179, 189; 73/23.2; 123/254; 222/1; 700/95

See application file for complete search history.

(56) References Cited

U.S. PATENT DOCUMENTS

| | | | |
|---|---|---|---|
| 4,397,958 A | 8/1983 | Vroom | |
| 5,569,922 A | 10/1996 | Clarke | |
| 5,611,307 A * | 3/1997 | Watson | 123/254 |
| 5,633,798 A * | 5/1997 | Kopp | 701/111 |
| 5,654,497 A * | 8/1997 | Hoffheins et al. | 73/23.2 |
| 5,956,254 A * | 9/1999 | Collins | 700/239 |
| 6,065,638 A * | 5/2000 | Terranova et al. | 222/1 |
| 6,155,101 A * | 12/2000 | Renault et al. | 73/35.02 |
| 6,983,186 B2 * | 1/2006 | Navani et al. | 700/95 |
| 7,925,449 B2 * | 4/2011 | Lutnick et al. | 702/23 |
| 2003/0023397 A1 | 1/2003 | Parlor et al. | |

OTHER PUBLICATIONS

USPTO Office Action for U.S. Appl. No. 11/856,900, Apr. 1, 2010 (19 pages).
USPTO Notice of Allowance and Fees Due for U.S. Appl. No. 11/856,900, Dec. 9, 2010 (7 pages).
International Search Report and Written Opinion for International Application No. PCT/US07/78729, mailed Mar. 28, 2008 (8 pages).
International Preliminary Report on Patentability for International Application No. PCT/US07/78729, mailed Mar. 24, 2009 (11 pages).
U.S. Appl. No. 60/845,343, filed Sep. 18, 2006, Lutnick.

* cited by examiner

*Primary Examiner* — Mohamed Charioui
*Assistant Examiner* — Felix Suarez
(74) *Attorney, Agent, or Firm* — Ruth J. Ma

(57) ABSTRACT

Products and processes are provided herewith for analyzing octane content in a fuel sample that include the step or steps of receiving an octane measurement of a fuel sample from a octane analyzer, rounding the octane measurement to a nearest recognized octane rating, comparing the rounded octane measurement with a listed octane rating for the fuel sample, and communicating results of the comparison to a user of the octane analyzer. The octane analyzer may be incorporated into a fuel pump or a vehicle. The results of the comparison may also be used to adjust the vehicle operating parameters to account for the actual octane rating of the fuel dispensed into the vehicle.

19 Claims, 2 Drawing Sheets

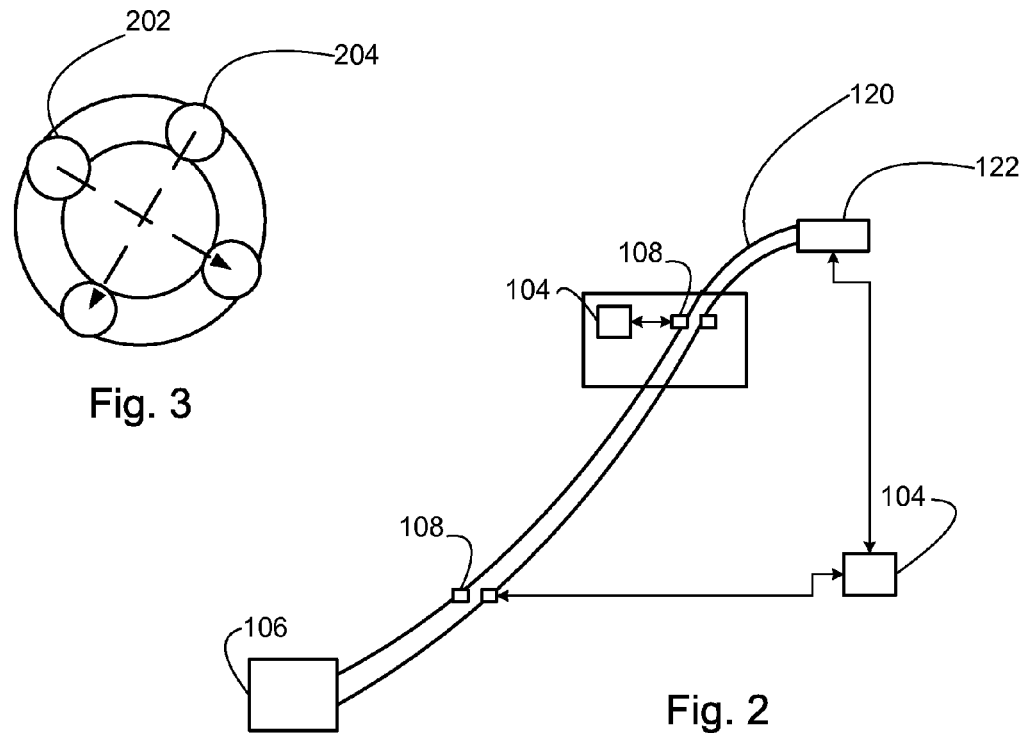
Fig. 3
Fig. 2
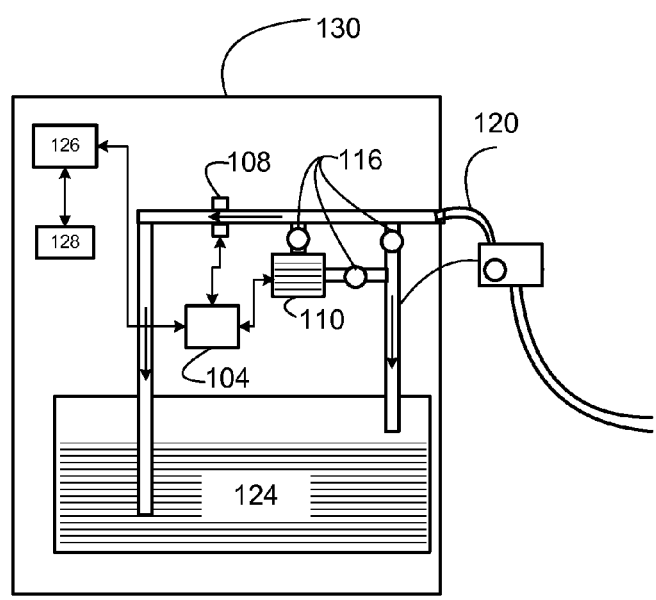
Fig. 4

PRODUCTS AND PROCESSES FOR ANALYZING OCTANE CONTENT

CROSS REFERENCE TO RELATED APPLICATIONS

The present application is a continuation of U.S. application Ser. No. 11/856,900, filed on Sep. 18, 2007 now U.S. Pat. No. 7,925,449, which claims priority to U.S. Provisional Application No. 60/845,343, filed on Sep. 18, 2006, all of which are incorporated by reference herein.

BRIEF DESCRIPTION OF THE DRAWINGS

The accompanying drawings are not intended to be drawn to scale. In the drawings, each identical or similar component that is illustrated in various figures is represented by a like numeral. For purposes of clarity, not every component may be labeled or act identified in every drawing. In the drawings:

FIG. 2 shows an octane analyzer incorporated into a fuel nozzle according to an embodiment of the systems disclosed herein;

FIG. 3 shows a cross section of a fuel conduit with emitters and receives oppositely disposed thereon according to an embodiment of the systems disclosed herein; and FIG. 4 shows an octane analyzer incorporated into a vehicle according to one embodiment of the systems disclosed herein.

DETAILED DESCRIPTION

Figure 1A:
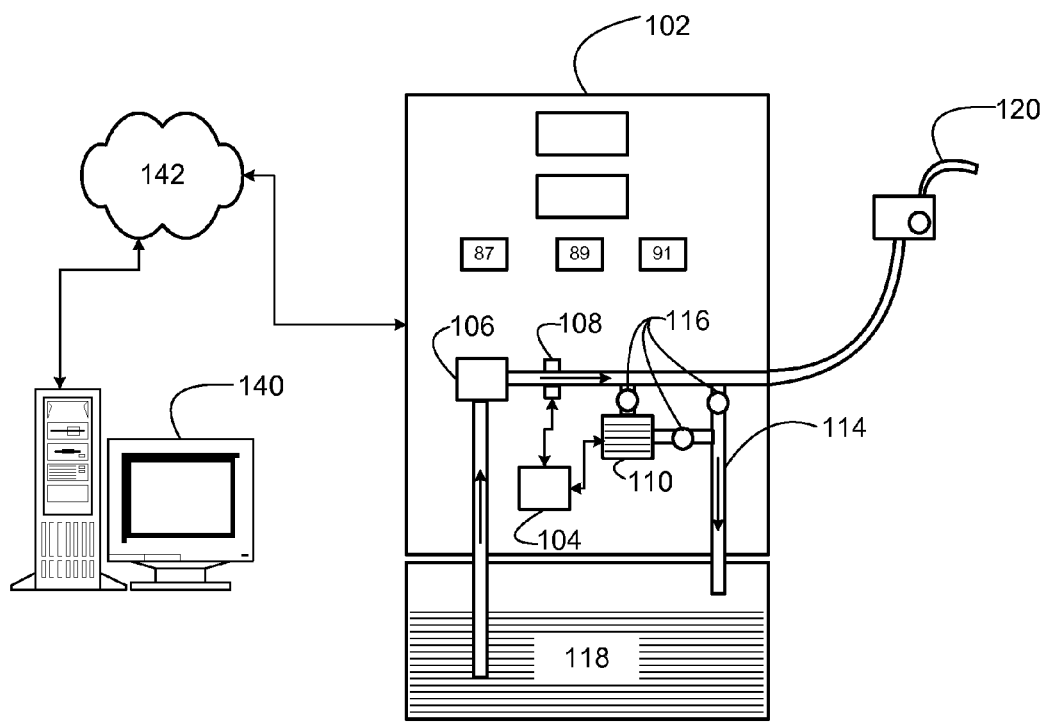
FIG. 1 shows an octane analyzer incorporated into a fuel pump according to an embodiment of the systems disclosed herein.

The following sections I-X provide a guide to interpreting the present application.

Terms

The term "product" means any machine, manufacture and/or composition of matter, unless expressly specified otherwise.

The term "process" means any process, algorithm, method or the like, unless expressly specified otherwise.

Each process (whether called a method, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

The term "invention" and the like mean "the one or more inventions disclosed in this application", unless expressly specified otherwise.

The terms "an embodiment", "embodiment", "embodiments", "the embodiment", "the embodiments", "one or more embodiments", "some embodiments", "certain embodiments", "one embodiment", "another embodiment" and the like mean "one or more (but not all) embodiments of the disclosed invention(s)", unless expressly specified otherwise.

The term "variation" of an invention means an embodiment of the invention, unless expressly specified otherwise.

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "plurality" means "two or more", unless expressly specified otherwise.

The term "herein" means "in the present application, including anything which may be incorporated by reference", unless expressly specified otherwise.

The phrase "at least one of", when such phrase modifies a plurality of things (such as an enumerated list of things) means any combination of one or more of those things, unless expressly specified otherwise. For example, the phrase "at least one of a widget, a car and a wheel" means either (i) a widget, (ii) a car, (iii) a wheel, (iv) a widget and a car, (v) a widget and a wheel, (vi) a car and a wheel, or (vii) a widget, a car and a wheel. The phrase "at least one of", when such phrase modifies a plurality of things does not mean "one of each of" the plurality of things.

Numerical terms such as "one", "two", etc. when used as cardinal numbers to indicate quantity of something (e.g., one widget, two widgets), mean the quantity indicated by that numerical term, but do not mean at least the quantity indicated by that numerical term. For example, the phrase "one widget" does not mean "at least one widget", and therefore the phrase "one widget" does not cover, e.g., two widgets.

The phrase "based on" does not mean "based only on", unless expressly specified otherwise. In other words, the phrase "based on" describes both "based only on" and "based at least on". The phrase "based at least on" is equivalent to the phrase "based at least in part on".

The term "represent" and like terms are not exclusive, unless expressly specified otherwise. For example, the term "represents" do not mean "represents only", unless expressly specified otherwise. In other words, the phrase "the data represents a credit card number" describes both "the data represents only a credit card number" and "the data represents a credit card number and the data also represents something else".

The term "whereby" is used herein only to precede a clause or other set of words that express only the intended result, objective or consequence of something that is previously and explicitly recited. Thus, when the term "whereby" is used in a claim, the clause or other words that the term "whereby" modifies do not establish specific further limitations of the claim or otherwise restricts the meaning or scope of the claim.

The term "e.g." and like terms mean "for example", and thus does not limit the term or phrase it explains. For example, in the sentence "the computer sends data (e.g., instructions, a data structure) over the Internet", the term "e.g." explains that "instructions" are an example of "data" that the computer may send over the Internet, and also explains that "a data structure" is an example of "data" that the computer may send over the Internet. However, both "instructions" and "a data structure" are merely examples of "data", and other things besides "instructions" and "a data structure" can be "data".

The term "respective" and like terms mean "taken individually". Thus if two or more things have "respective" characteristics, then each such thing has its own characteristic, and these characteristics can be different from each other but need not be. For example, the phrase "each of two machines has a respective function" means that the first such machine has a function and the second such machine has a function as well. The function of the first machine may or may not be the same as the function of the second machine.

The term "i.e." and like terms mean "that is", and thus limits the term or phrase it explains. For example, in the sentence "the computer sends data (i.e., instructions) over the Internet", the term "i.e." explains that "instructions" are the "data" that the computer sends over the Internet.

Any given numerical range shall include whole and fractions of numbers within the range. For example, the range "1 to 10" shall be interpreted to specifically include whole numbers between 1 and 10 (e.g., 1, 2, 3, 4, . . . 9) and non-whole numbers (e.g., 1.1, 1.2, . . . 1.9).

Where two or more terms or phrases are synonymous (e.g., because of an explicit statement that the terms or phrases are synonymous), instances of one such term/phrase does not mean instances of another such term/phrase must have a different meaning. For example, where a statement renders the meaning of "including" to be synonymous with "including but not limited to", the mere usage of the phrase "including but not limited to" does not mean that the term "including" means something other than "including but not limited to".

II. Determining

The term "determining" and grammatical variants thereof (e.g., to determine a price, determining a value, determine an object which meets a certain criterion) is used in an extremely broad sense. The term "determining" encompasses a wide variety of actions and therefore "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing, and the like.

The term "determining" does not imply certainty or absolute precision, and therefore "determining" can include estimating, extrapolating, predicting, guessing and the like.

The term "determining" does not imply that mathematical processing must be performed, and does not imply that numerical methods must be used, and does not imply that an algorithm or process is used.

The term "determining" does not imply that any particular device must be used. For example, a computer need not necessarily perform the determining.

III. Forms of Sentences

Where a limitation of a first claim would cover one of a feature as well as more than one of a feature (e.g., a limitation such as "at least one widget" covers one widget as well as more than one widget), and where in a second claim that depends on the first claim, the second claim uses a definite article "the" to refer to the limitation (e.g., "the widget"), this does not imply that the first claim covers only one of the feature, and this does not imply that the second claim covers only one of the feature (e.g., "the widget" can cover both one widget and more than one widget).

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device, article or other product is described herein, more than one device/article (whether or not they cooperate) may alternatively be used in place of the single device/article that is described. Accordingly, the functionality that is described as being possessed by a device may alternatively be possessed by more than one device/article (whether or not they cooperate).

Similarly, where more than one device, article or other product is described herein (whether or not they cooperate), a single device/article may alternatively be used in place of the more than one device or article that is described. For example, a plurality of computer-based devices may be substituted with a single computer-based device. Accordingly, the various functionality that is described as being possessed by more than one device or article may alternatively be possessed by a single device/article.

The functionality and/or the features of a single device that is described may be alternatively embodied by one or more other devices which are described but are not explicitly described as having such functionality/features. Thus, other embodiments need not include the described device itself, but rather can include the one or more other devices which would, in those other embodiments, have such functionality/features.

IV. Disclosed Examples and Terminology are Not Limiting

Neither the Title (set forth at the beginning of the first page of the present application) nor the Abstract (set forth at the end of the present application) is to be taken as limiting in any way as the scope of the disclosed invention(s). An Abstract has been included in this application merely because an Abstract of not more than 150 words is required under 37 C.F.R. §1.72(b).

The title of the present application and headings of sections provided in the present application are for convenience only, and are not to be taken as limiting the disclosure in any way.

Numerous embodiments are described in the present application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

No embodiment of method steps or product elements described in the present application constitutes the invention claimed herein, or is essential to the invention claimed herein, or is coextensive with the invention claimed herein, except where it is either expressly stated to be so in this specification or expressly recited in a claim.

The preambles of the claims that follow recite purposes, benefits and possible uses of the claimed invention only and do not limit the claimed invention.

The present disclosure is not a literal description of all embodiments of the invention(s). Also, the present disclosure is not a listing of features of the invention(s) which must be present in all embodiments.

Devices that are described as in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for long period of time (e.g. weeks at a time). In addition, devices that are in communication with each other may communicate directly or indirectly through one or more intermediaries.

A description of an embodiment with several components or features does not imply that all or even any of such components/features are required. On the contrary, a variety of optional components are described to illustrate the wide variety of possible embodiments of the present invention(s). Unless otherwise specified explicitly, no component/feature is essential or required.

Although process steps, algorithms or the like may be described or claimed in a particular sequential order, such processes may be configured to work in different orders. In other words, any sequence or order of steps that may be explicitly described or claimed does not necessarily indicate a requirement that the steps be performed in that order. The steps of processes described herein may be performed in any order possible. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention(s), and does not imply that the illustrated process is preferred.

Although a process may be described as including a plurality of steps, that does not imply that all or any of the steps are preferred, essential or required. Various other embodiments within the scope of the described invention(s) include other processes that omit some or all of the described steps. Unless otherwise specified explicitly, no step is essential or required.

Although a process may be described singly or without reference to other products or methods, in an embodiment the process may interact with other products or methods. For example, such interaction may include linking one business model to another business model. Such interaction may be provided to enhance the flexibility or desirability of the process.

Although a product may be described as including a plurality of components, aspects, qualities, characteristics and/or features, that does not indicate that any or all of the plurality are preferred, essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

An enumerated list of items (which may or may not be numbered) does not imply that any or all of the items are equivalent to each other or readily substituted for each other.

All embodiments are illustrative, and do not imply that the invention or any embodiments were made or performed, as the case may be.

V. Computing

It will be readily apparent to one of ordinary skill in the art that the various processes described herein may be implemented by, e.g., appropriately programmed general purpose computers, special purpose computers and computing devices. Typically a processor (e.g., one or more microprocessors, one or more microcontrollers, one or more digital signal processors) will receive instructions (e.g., from a memory or like device), and execute those instructions, thereby performing one or more processes defined by those instructions. Instructions may be embodied in, e.g., one or more computer programs, one or more scripts.

A "processor" means one or more microprocessors, central processing units (CPUs), computing devices, microcontrollers, digital signal processors, or like devices or any combination thereof, regardless of the architecture (e.g., chip-level multiprocessing/multi-core, RISC, CISC, Microprocessor without Interlocked Pipeline Stages, pipelining configuration, simultaneous multithreading).

Thus a description of a process is likewise a description of an apparatus for performing the process. The apparatus that performs the process can include, e.g., a processor and those input devices and output devices that are appropriate to perform the process.

Further, programs that implement such methods (as well as other types of data) may be stored and transmitted using a variety of media (e.g., computer readable media) in a number of manners. In some embodiments, hard-wired circuitry or custom hardware may be used in place of, or in combination with, some or all of the software instructions that can implement the processes of various embodiments. Thus, various combinations of hardware and software may be used instead of software only.

The term "computer-readable medium" refers to any medium, a plurality of the same, or a combination of different media, that participate in providing data (e.g., instructions, data structures) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols, such as Ethernet (or IEEE 802.3), SAP, ATP, Bluetooth™, and TCP/IP, TDMA, CDMA, and 3G; and/or (iv) encrypted to ensure privacy or prevent fraud in any of a variety of ways well known in the art.

Thus a description of a process is likewise a description of a computer-readable medium storing a program for performing the process. The computer-readable medium can store (in any appropriate format) those program elements which are appropriate to perform the method.

Just as the description of various steps in a process does not indicate that all the described steps are required, embodiments of an apparatus include a computer/computing device operable to perform some (but not necessarily all) of the described process.

Likewise, just as the description of various steps in a process does not indicate that all the described steps are required, embodiments of a computer-readable medium storing a program or data structure include a computer-readable medium storing a program that, when executed, can cause a processor to perform some (but not necessarily all) of the described process.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models and/or distributed databases) could be used to store and manipulate the data types described herein. Likewise, object methods or behaviors of a database can be used to implement various processes, such as the described herein. In addition, the databases may, in a known manner, be stored locally or remotely from a device which accesses data in such a database.

Various embodiments can be configured to work in a network environment including a computer that is in communication (e.g., via a communications network) with one or more devices. The computer may communicate with the devices directly or indirectly, via any wired or wireless medium (e.g. the Internet, LAN, WAN or Ethernet, Token Ring, a telephone line, a cable line, a radio channel, an optical communications line, commercial on-line service providers, bulletin board systems, a satellite communications link, a combination of any of the above). Each of the devices may themselves comprise computers or other computing devices, such as those based on the Intel® Pentium® or Centrino™ processor, that are adapted to communicate with the computer. Any number and type of devices may be in communication with the computer.

In an embodiment, a server computer or centralized authority may not be necessary or desirable. For example, the present invention may, in an embodiment, be practiced on one or more devices without a central authority. In such an embodiment, any functions described herein as performed by the server computer or data described as stored on the server computer may instead be performed by or stored on one or more such devices.

Where a process is described, in an embodiment the process may operate without any user intervention. In another embodiment, the process includes some human intervention (e.g., a step is performed by or with the assistance of a human).

VI. Continuing Applications

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application.

Applicants intend to file additional applications to pursue patents for subject matter that has been disclosed and enabled but not claimed in the present application.

VII. 35 U.S.C. §112, Paragraph 6

In a claim, a limitation of the claim which includes the phrase "means for" or the phrase "step for" means that 35 U.S.C. §112, paragraph 6, applies to that limitation.

In a claim, a limitation of the claim which does not include the phrase "means for" or the phrase "step for" means that 35 U.S.C. §112, paragraph 6 does not apply to that limitation, regardless of whether that limitation recites a function without recitation of structure, material or acts for performing that function. For example, in a claim, the mere use of the phrase "step of" or the phrase "steps of" in referring to one or more steps of the claim or of another claim does not mean that 35 U.S.C. §112, paragraph 6, applies to that step(s).

With respect to a means or a step for performing a specified function in accordance with 35 U.S.C. §112, paragraph 6, the corresponding structure, material or acts described in the specification, and equivalents thereof, may perform additional functions as well as the specified function.

Computers, processors, computing devices and like products are structures that can perform a wide variety of functions. Such products can be operable to perform a specified function by executing one or more programs, such as a program stored in a memory device of that product or in a memory device which that product accesses. Unless expressly specified otherwise, such a program need not be based on any particular algorithm, such as any particular algorithm that might be disclosed in the present application. It is well known to one of ordinary skill in the art that a specified function may be implemented via different algorithms, and any of a number of different algorithms would be a mere design choice for carrying out the specified function.

Therefore, with respect to a means or a step for performing a specified function in accordance with 35 U.S.C. §112, paragraph 6, structure corresponding to a specified function includes any product programmed to perform the specified function. Such structure includes programmed products which perform the function, regardless of whether such product is programmed with (i) a disclosed algorithm for performing the function, (ii) an algorithm that is similar to a disclosed algorithm, or (iii) a different algorithm for performing the function.

Where there is recited a means for performing a function that is a method, one structure for performing this method includes a computing device (e.g., a general purpose computer) that is programmed and/or configured with appropriate hardware to perform that function.

Also includes a computing device (e.g., a general purpose computer) that is programmed and/or configured with appropriate hardware to perform that function via other algorithms as would be understood by one of ordinary skill in the art.

VIII. Disclaimer

Numerous references to a particular embodiment does not indicate a disclaimer or disavowal of additional, different embodiments, and similarly references to the description of embodiments which all include a particular feature does not indicate a disclaimer or disavowal of embodiments which do not include that particular feature. A clear disclaimer or disavowal in the present application shall be prefaced by the phrase "does not include" or by the phrase "cannot perform".

IX. Incorporation by Reference

Any patent, patent application or other document referred to herein is incorporated by reference into this patent application as part of the present disclosure, but only for purposes of written description in accordance with 35 U.S.C. §112, paragraph 1 and enablement in accordance with 35 U.S.C. §112, paragraph 1, and should in no way be used to limit, define, or otherwise construe any term of the present application where the present application, without such incorporation by reference, would not have failed to provide an ascertainable meaning, but rather would have allowed an ascertainable meaning for such term to be provided. Thus, the person of ordinary skill in the art need not have been in any way limited by any embodiments provided in the reference Any incorporation by reference does not, in and of itself, imply any endorsement of, ratification of or acquiescence in any statements, opinions, arguments or characterizations contained in any incorporated patent, patent application or other document, unless explicitly specified otherwise in this patent application.

X. Prosecution History

In interpreting the present application (which includes the claims), one of ordinary skill in the art shall refer to the prosecution history of the present application, but not to the prosecution history of any other patent or patent application, regardless of whether there are other patent applications that are considered related to the present application, and regardless of whether there are other patent applications that share a claim of priority with the present application.

XI. Overview

Disclosed herein are various systems and processes that permit the octane content of gasoline to be determined or verified by an individual, e.g., at a gasoline or other fuel pump. This can be advantageous since a higher-octane fuel is frequently preferred, but is more expensive. Thus there can be various incentives to actually provide a lower-octane fuel than advertised.

XII. Octane Measurement Methods

The octane number does not correspond to the concentration of any one constituent in the fuel, but rather to the pre-ignition properties of the fuel as compared with standard fuel mixtures. The octane rating is a measure of the autoignition resistance of gasoline (petrol) and other fuels used in spark-ignition internal combustion engines. Octane is measured relative to a mixture of isooctane (2,2,4-trimethylpentane, an isomer of octane) and n-heptane. For example, an 87-octane gasoline has the same knock resistance as a mixture of 87 vol-% isooctane and 13 vol-% n-heptane. However, this does not mean that the gasoline actually should contain these chemicals in these proportions—merely that the gasoline has the same autoignition resistance as the described mixture. A high tendency to autoignite, or low octane rating, is undesirable in a gasoline engine (but desirable in a diesel engine).

The most common type of octane rating worldwide is the Research Octane Number (RON). RON is determined by running the fuel through a specific test engine with a variable compression ratio under controlled conditions, and comparing these results with those for mixtures of isooctane and n-heptane. Another type of octane rating, referred to as the Motor Octane Number (MON) or the aviation lean octane rating, is generally considered a better measure of how the fuel behaves when under load. MON testing uses a similar test engine to that used in RON testing, but with a preheated fuel mixture, a higher engine speed, and variable ignition timing to further stress the fuel's knock resistance. Depending on the composition of the fuel, the MON of a modem gasoline will be about 8 to 10 points lower than the RON. Normally fuel specifications require both a minimum RON and a minimum MON.

In most countries (including all of Europe and Australia) the "headline" octane that is shown on the pump is the RON, but in the United States and some other countries the headline number is the average of the RON and the MON, sometimes called the Anti-Knock Index (AKI), Road Octane Number (RdON), Pump Octane Number (PON), or (R+M)/2. Because of the 8 to 10 point difference referenced above, the listed octane in the United States will be about 4 to 5 points lower than that listed for the same fuel elsewhere. For example, 87 octane fuel, the "regular" gasoline in the US and Canada, would be considered 91-95 (regular) in Europe. The octane rating may also be a "trade name", with the actual figure being higher than the nominal rating.

XIII. Effects of Octane Rating

Higher octane ratings correlate to higher activation energies. Activation energy is the amount of energy necessary to start a chemical reaction. Since higher octane fuels have higher activation energies, it is less likely that a given compression will cause knocking. Knocking can damage an engine. Lower-octane gas (e.g., 87-octane gasoline) can handle the least amount of compression before igniting.

Compression is directly related to power (see engine tuning), so engines that require higher octane usually deliver more power. Engine power is a function of the fuel as well as the engine design and is related to octane ratings of the fuel. Power is limited by the maximum amount of fuel-air mixture that can be forced into the combustion chamber. At partial load, only a small fraction of the total available power is produced because the manifold is operating at pressures far below atmospheric. In this case, the octane requirement is far lower than what is available. It is only when the throttle is opened fully and the manifold pressure increases to atmospheric (or higher in the case of supercharged or turbocharged engines) that the full octane requirement is achieved.

Many high-performance engines are designed to operate with a high maximum compression and thus need a high quality (high energy) fuel usually associated with high octane numbers and thus demand high-octane premium gasoline.

Engines perform best when using fuel with the octane rating they were designed for. There can possibly be a minimal increase in performance by using a fuel with a different octane rating.

XIV. Portable Octane Analyzers

In an embodiment, a portable octane analyzer is provided that allows a non-technically skilled user to determine whether the listed octane rating matches the actual octane rating of gasoline being dispensed. The octane analyzer may include a processor and a memory with software stored or embodiment therein that enable the device to receive a signal from a receiver representing spectra from a fuel sample, e.g., IR light after being absorbed and scattered through the sample, compare the signal with that of a known sample, and determine therefrom the octane rating of the fuel sample. In an embodiment, a portable octane analyzer displays a rating (e.g., two digits such as "87") corresponding to the closest integral octane rating. In an embodiment, a portable octane analyzer displays a rating corresponding to the closest of a set of typically available octane ratings (e.g., the displayed rating is one of "87", "89", "91" and possibly "none"). That is, the device may measure the octane rating of a fuel and round the measurement to the nearest recognized two digit octane rating. For example, a measurement of 86.95 may be rounded to 87. Similarly, a reading of 89.55 may be rounded to 89. In an embodiment, the user may enter an expected octane rating, and the portable octane analyzer displays whether the analyzed fluid meets the expected octane rating (the displayed rating is one of "pass" and "fail", the displayed rating is one of "pass", "exceed" and "fail"). The display need not be numeric or alphanumeric. For example, the display can be graphical (a bar graph, a line chart, one of two bubbles filled in).

The ZX-101 C portable octane analyzer (provided by Zeltex, Inc. of Hagerstown, Md.) permits analysis of the octane content of gasoline (a sample of approximately eight ounces). The ZX-101 C portable octane analyzer allows non-technically skilled users to provide octane measurements in about 20 seconds. The octane rating according to any of the [(R+M)/2], ROM and MON methodologies can be determined. The ZX-101 C portable octane analyzer includes a built-in printer and an LCD display, and can connect via a RS-232 output.

A device such as the ZX-101 C portable octane analyzer can be modified, adapted or enhanced to provide a display as described herein. For example, in an embodiment, the software/firmware that drives the LCD display can be modified to display the octane-related data in any manner described herein by converting or translating the data that the ZX-101 C would normally output. In an embodiment, another display or another device can be connected to the RS-232 port (or another port) of the ZX-101 C in order to convert or translate the data that the ZX-101 C would normally output into any manner described herein.

XV. Analyzer Integrated Into Pump

Referring to FIG. 1a, in an embodiment, the gasoline pump 102 can receive the portable octane analyzer 104, and the portable octane analyzer 104 can analyze the stream of gasoline being dispensed before the gasoline leaves the pump, e.g., at any point 108 past the pumping mechanism 106. The pump can include a recession or other area which defines a shape for receiving a portable octane analyzer 104 or receiving a portion thereof which receives a fluid sample. The portable octane analyzer can be removably placed into the area, and thus placed in fluid communication with the stream, allowing the stream to be analyzed.

Figure 1B:
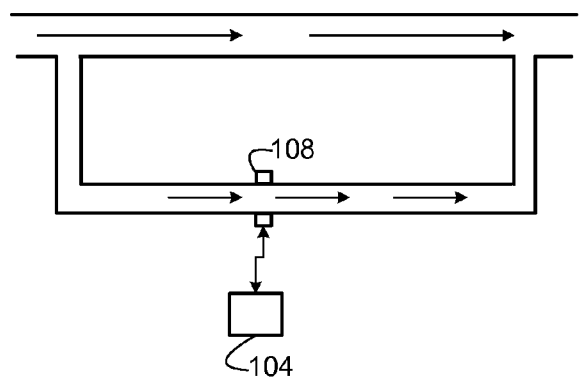

In an embodiment, the pump can include such an octane analyzer which is not removable, but is affixed to the pump. The fuel pump or any other device comprising the octane analyzer may include piping in parallel, with or without valves to reduce flow in at least one of the pipes, which allows dual stream flows during fueling; one with a first flow and a second with a second flow lesser than the first flow, as shown in FIG. 1b. In this instance, the measurement may result in a more accurate reading with the slower flow than the higher flow. Alternatively or additionally, in an embodiment, the pump 102 may include a receptacle 110 with an inlet 112 and outlet 114 that allows fuel dispensed during a pumping session to enter and exit the receptacle 110, respectively. In this instance, the pump may include one or more valve mechanisms 116 switched, e.g., by the pump 102, in such a manner to allow fuel to enter automatically into the receptacle 110 at some time during initial pumping for a sufficient time to at least partially fill the receptacle 110 for the analyzer 104 to measure the octane rating of the fuel in the receptacle 110. The valve mechanisms 116 preferably block or significantly reduce fuel flow through the receptacle for at least the time of the reading. Once the reading has been taken, the valve mechanisms 116 preferably open automatically to allow the fuel to exit the receptacle 310 for the next reading. This may be accomplished by pumping the standing fuel into the vehicle or allowing the fuel to drain back into the tank 118. The process may be repeated during the pumping session to obtain multiple readings during the session. An average or a median reading, or any other statistical value may be derived from the multiple readings.

XVI. Analyzer Integrated Into Nozzle

Referring back to FIG. 2, similarly, in an embodiment, the nozzle 120 of the gasoline pump can receive the portable octane analyzer 104, and the portable octane analyzer can analyze the stream of gasoline being dispensed as the gasoline passes through or leaves the nozzle 120. The nozzle 120 can include a recession or other area which defines a shape for receiving a portable octane analyzer or receiving a portion thereof which receives a fluid sample. The portable octane analyzer can be removably placed into the area, and thus placed in fluid communication with the stream, allowing the stream to be analyzed. In an embodiment, the nozzle can include such an octane analyzer 104 which is not removable, but is affixed to the nozzle.

In an embodiment, the portion of the analyzer that receives the fuel stream sample includes a collar 122 that is placed over the pump nozzle 120. Referring to FIG. 3, the collar preferably includes at least one near IR emitter 202 and at least one near IR receiver 204. A plurality of emitters 202 may be disposed circumferentially on the collar opposite the receivers 204. The emitters and receivers may be the actual emitters/receivers or near IR fiber optic extensions thereof. In the later, the emitters and receivers may be remote from the pump nozzle 120. it is understood that the emitters/receivers may be disposed on any conduit through which fuel is being dispensed. Alternatively or additionally, the nozzle may include parallel piping and/or a reservoir as discussed above.

XVII. Analyzer Integrated Into Vehicle

Referring to FIG. 4, in an embodiment, the vehicle 130 can include an octane analyzer 104. The vehicle 130 may include a receptacle 110 with an inlet 112 and outlet 114 that allows fuel dispensed during a pumping session to enter and exit the receptacle 110, respectively, as well as one or more valve mechanisms 116 switched, e.g., by the vehicle 130, in such a manner to allow fuel to enter automatically into the receptacle 110 at some time during initial pumping for a sufficient time to at least partially fill the receptacle 110 for the analyzer 104 to measure the octane rating of the fuel in the receptacle 110. The valve mechanisms 116 may block or significantly reduce fuel flow as discussed above for at least the time for taking the reading. Once the reading has been taken, the valve mechanisms 116 may open automatically to allow the fuel to exit the receptacle 310 and drain into the fuel tank 124. The reading may be communicated to the ECU and/or the driver as disclosed herein. The ECU may adjust the engine parameters to account for the octane reading. That is, the ECU may retard the engine ignition timing based on a lower than required octane measurement. The timing may be retarded sufficient to prevent pre-ignition based on the octane reading. For example, in a vehicle that requires 91 octane fuel, a reading of 89 may cause the ECU to retard ignition timing by 1-10 degrees. The timing may similarly be advanced to account for a better than expected octane measurement. The vehicle 130 may also sample the fuel in the tank 124 and retard or advance ignition timing or any other engine parameter based on the reading. This may be accomplished by periodically pumping fuel from the tank 124 into the receptacle 110. Alternatively, the octane analyzer 104 may take a reading directly from the tank 124. This may be accomplished with emitters/receivers disposed on the vehicle fuel pump pickup or other piping similar to that of the collar embodiment described above. Engine parameters may be adjusted based on the rounded measurements or the actual measurements.

XVIII. Compensation for Erroneous Octane Rating

In an embodiment, erroneous instances of octane rating (or instances where the listed octane number is higher than the measured octane number) may be deemed compensable (e.g., by the merchant selling the fuel). In such an embodiment, instances of an erroneous octane rating may require verification (e.g., retesting by the same octane analyzer, testing by another octane analyzer) before compensation is due. Verification may also be by another octane analyzer during a subsequent fuel sale for the same grade of fuel. Compensation can be by way of, e.g., cash payment of a fee ($10 per instance, $1.00 per gallon of fuel purchased, etc.). Compensation may also be the difference between the cost of the fuel with the listed octane and that of the fuel with the measured octane. Multiple instances by the same merchant or by multiple outlets (e.g., franchisees) of the same brand (e.g., different Texaco gasoline stations) can be compensated at even greater amounts, such as by a predetermined factor of, e.g., 1.5-3.0, etc. Compensation for the erroneous octane rating may be by a reduction in the sale price at the time of the sale or at some later time, such as with a credit to a credit card payment, e.g., after verification. In instances where the measurement yields better than expected octane, the higher than expected measurement may be displayed to the user, e.g., the consumer. The better than expected results may not require that the consumer provide additional compensation to the merchant.

XIX. Audit Trail for Erroneous Octane Rating

Gasoline pumps can be placed in communication with one or more servers 140 via a network 142 (e.g., a wireless and/or a wired network). Each pump can have a unique and unfalsifiable identifier (e.g., provided by a server). Similarly, octane analyzers can include unique and unfalsifiable identifiers, and can encrypt its readings and other information.

The octane analyzer 104, when in communication with the pump 102, can authenticate the pump 102 that the octane reading was taken from. If the analyzer receives an invalid identifier then the analyzer knows the reading is in error.

The pump 102 can also record and send to the server 140 the gasoline grade it purportedly dispensed, and when (e.g., for each sale, the times of dispensing and the volumes dispensed are each measured and recorded). The pump 102 may also receive the measurement from the analyzer 104, internally or otherwise, and communicate the measurement to the server 140.

Thus, if the user of the octane analyzer 104 desires to report an erroneous octane rating, the analyzer's recorded information can be compared with the recorded information of the pump to determine whether there was in fact an erroneous octane rating in gasoline dispensed at the pump.

XX. Other Embodiments

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of instant invention. Accordingly, the foregoing description and drawings are by way of example only.

What is claimed is:

1. A method comprising:
   determining, using a portable octane analyzer, a first octane measurement at a first nozzle,
      wherein the octane analyzer is removeably attachable to the first nozzle; and
      wherein the first octane measurement measures a fuel sample that is being dispensed from a fuel pump;
   determining, using the portable octane analyzer, a second octane measurement at a second nozzle, wherein the second octane measurement measures a fuel sample that is being dispensed from a different fuel pump;
   comparing, using the portable octane analyzer, the first octane measurement and the second octane measurement with at least one standard octane rating;
   determining, using the portable octane analyzer, that the first octane measurement fails to match the at least one standard octane rating;
   transmitting, via the portable octane analyzer to a user, an indication of an error in the first octane measurement; and
   displaying, on a display, the indication of the error.

2. The method of claim 1 further comprising:
   displaying on a display a message comprising at least one of:
      an indication of a pass,
      an indication of a fail, and
      an indication that a threshold has been exceeded.

3. The method of claim 1 further comprises:
   re-measuring the octane measurement of the fuel sample, in response to the determination that the first octane measurement fails to match the standard octane rating.

4. The method of claim 1, wherein the octane analyzer comprises a collar that is removably disposed over one of the first nozzle and the second nozzle,
   wherein the collar comprises at least one infrared (IR) emitter and the at least one infrared (IR) receiver disposed circumferentially about the collar,
   wherein the at least one IR emitter transmits octane measurements to the at least one IR receiver.

5. The method of claim 1, wherein the octane analyzer comprises a power supply that is portable.

6. The method of claim 1, wherein the octane analyzer does not share a power supply with the fuel pump.

7. The method of claim 1 further comprising:
   computing, via the octane analyzer, a compensation for the user, based in part on the error; and
   reducing a price of fuel based on the compensation.

8. The method of claim 7, wherein the act of computing the compensation further comprises:
   determining a first cost of the fuel sample at the standard octane rating;
   determining a second cost of the fuel sample at the first octane measurement; and
   calculating a difference between the first cost and the second cost.

9. The method of claim 1, wherein the second nozzle is separate from the fuel pump of the first nozzle.

10. The method of claim 1, wherein the second nozzle is at a location that is separate from the first nozzle's location.

11. The method of claim 1 further comprising:
rounding, using the portable octane analyzer, each of the first octane measurement and the second octane measurement to a nearest recognized octane rating.

12. The method of claim 1 further comprising:
displaying, on the display, at least one of the first octane measurement and the second octane measurement.

13. The method of claim 1 further comprising:
simultaneously displaying, on the display, the first octane measurement and the second octane measurement.

14. The method of claim 1 further comprising:
adjusting a vehicle ignition timing based on at least one of the first octane measurement and the second octane measurement.

15. The method of claim 1, wherein the fuel pump comprises an identifier that is unique to the fuel pump.

16. The method of claim 15 further comprising:
prior to measuring the octane measurement, determining that the identifier of the fuel pump is valid.

17. The method of claim 1, wherein the octane analyzer is capable of encrypting the first octane measurement and the second octane measurement.

18. A method comprising:
determining, using a portable octane analyzer, a first octane measurement at a first nozzle,
wherein the octane analyzer comprises a collar that is removably disposed over one of the first nozzle and the second nozzle,
wherein the collar comprises: at least one infrared (IR) emitter; and at least one IR receiver disposed circumferentially about the collar, wherein the at least one IR emitter transmits octane measurements to the at least one IR receiver,
wherein the first octane measurement measures a fuel sample that is being dispensed from a fuel pump;
determining, using the portable octane analyzer, a second octane measurement at a second nozzle, wherein the second octane measurement measures a fuel sample that is being dispensed from a different fuel pump;
comparing, using the portable octane analyzer, the first octane measurement and the second octane measurement with at least one standard octane rating; and
determining, using the portable octane analyzer, that the first octane measurement fails to match the at least one standard octane rating;
transmitting, via the portable octane analyzer to a user, an indication of an error in the first octane measurement;
displaying, on a display, the indication of the error;
computing, via the octane analyzer, a compensation for the user, based in part on the error; and
reducing a price of fuel based on the compensation.

19. A method comprising:
determining, using a portable octane analyzer, a first octane measurement at a first nozzle,
wherein the octane analyzer is removeably attachable to the first nozzle, and
wherein the first octane measurement measures a fuel sample that is being dispensed from a fuel pump;
determining, using the portable octane analyzer, a second octane measurement at a second nozzle, wherein the second octane measurement measures a fuel sample that is being dispensed from a different fuel pump;
comparing, using the portable octane analyzer, the first octane measurement and the second octane measurement with at least one standard octane rating; and
determining, using the portable octane analyzer, that the first octane measurement fails to match the at least one standard octane rating;
transmitting, via the portable octane analyzer to a user, an indication of an error in the first octane measurement;
displaying, on a display, the indication of the error;
computing, via the octane analyzer, a compensation for the user, based in part on the error; and
reducing a price of fuel based on the compensation.

* * * * *